US00PP27507P2

(12) United States Plant Patent
Oostveen

(10) Patent No.: US PP27,507 P2
(45) Date of Patent: Dec. 27, 2016

(54) ***HIBISCUS* PLANT NAMED 'EXTRHOPIN2'**

(50) Latin Name: *Hibiscus moscheutos*
Varietal Denomination: Extrhopin2

(71) Applicant: Cornelis A. Oostveen, De Kwakel (NL)

(72) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 0 days.

(21) Appl. No.: 14/545,810

(22) Filed: Jun. 23, 2015

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'Extrhopin2', characterized by its relatively compact, upright and somewhat outwardly spreading plant form; moderately vigorous growth habit; palmately-lobed leaves; large dark pink-colored flowers with red-colored centers; and good flower longevity.

2 Drawing Sheets

Botanical designation: *Hibiscus moscheutos*.
Cultivar denomination: 'EXTRHOPIN2'.

BACKGROUND OF THE INVENTION

The present invention relates to a new and distinct cultivar of *Hibiscus* plant, botanically known as *Hibiscus moscheutos*, commonly referred to as crimson-eyed rosemallow and hereinafter referred to by the name 'Extrhopin2'.

The new *Hibiscus* plant is a product of a planned breeding program conducted by the Inventor in De Kwakel, The Netherlands. The objective of the breeding program is to create new compact *Hibiscus* plants with resistance to insect pests.

The new *Hibiscus* plant originated from a cross-pollination in September, 2012 in De Kwakel, The Netherlands of a proprietary selection of *Hibiscus moscheutos* identified as code number CB1243, not patented, as the female, or seed, parent with *Hibiscus moscheutos* 'Oak Red', disclosed in U.S. Plant Pat. No. 21,875, as the male, or pollen, parent. The new *Hibiscus* plant was discovered and selected by the Inventor as a single flowering plant from within the progeny of the stated cross-pollination in a controlled greenhouse environment in De Kwakel, The Netherlands in August, 2013.

Asexual reproduction of the new *Hibiscus* plant by vegetative tip cuttings in a controlled greenhouse environment in De Kwakel, The Netherlands since September, 2013 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Extrhopin2'. These characteristics in combination distinguish 'Extrhopin2' as a new and distinct *Hibiscus* plant:

1. Relatively compact, upright and somewhat outwardly spreading plant form.
2. Moderately vigorous growth habit.
3. Palmately-lobed leaves.
4. Large dark pink-colored flowers with red-colored centers.
5. Good flower longevity.

Plants of the new *Hibiscus* can be compared to plants of the female parent selection. Plants of the new *Hibiscus* differ primarily from plants of the female parent selection in the following characteristics:

1. Leaves of plants of the new *Hibiscus* are palmately-lobed whereas leaves of plants of the female parent selection are not palmately-lobed.
2. Plants of the new *Hibiscus* and the female parent selection differ in flower color as plants of the female parent selection have lighter pink-colored flowers.

Plants of the new *Hibiscus* can be compared to plants of the male parent, 'Oak Red'. Plants of the new *Hibiscus* differ primarily from plants of 'Oak Red' in the following characteristics:

1. Plants of the new *Hibiscus* have lighter green-colored leaves than plants of 'Oak Red'.
2. Plants of the new *Hibiscus* and 'Oak Red' differ in flower color as plants of 'Oak Red' have red-colored flowers.

Plants of the new *Hibiscus* can be compared to plants of *Hibiscus moscheutos* 'Extrepink', disclosed in U.S. Plant Pat. No. 23,130. In side-by-side comparisons conducted in De Kwakel, The Netherlands, plants of the new *Hibiscus* differed primarily from plants of 'Extrepink' in the following characteristics:

1. Plants of the new *Hibiscus* were more compact than plants of 'Extrepink'.

2. Plants of the new *Hibiscus* had stronger lateral branches than plants of 'Extrepink'.
3. Leaves of plants of the new *Hibiscus* were palmately-lobed whereas leaves of plants of 'Extrepink' were not palmately-lobed.
4. Plants of the new *Hibiscus* and 'Extrepink' differed in flower color as plants of 'Extrepink' had lighter pink-colored flowers with lighter-colored centers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Extrhopin2' grown in a container.

The photograph on-the second sheet is a close-up view of a typical flower of 'Extrhopin2'.

DETAILED BOTANICAL DESCRIPTION

The aforementioned photographs and following observations, measurements and values describe plants grown during the late summer in 21-cm containers in a glass-covered greenhouse in De Kwakel, The Netherlands and under cultural practices typical of commercial *Hibiscus* production. During the production of the plants, day temperatures ranged from 18° C. to 33° C. and night temperatures ranged from 18° C. to 25° C. Plants were 16 weeks old when the photographs and the description were taken. In the following description, color references are made to The Royal Horticultural Society Colour Chart, 2007 Edition, except where general terms of ordinary dictionary significance are used.

Botanical classification: *Hibiscus moscheutos* 'Extrhopin2'.

Parentage:

*Female, or seed, parent.*—Proprietary selection of *Hibiscus moscheutos* identified as code number CB1243, not patented.

*Male or pollen parent.*—*Hibiscus moscheutos* 'Oak Red', disclosed in U.S. Plant Pat. No. 21,875.

Propagation:

*Type.*—By vegetative tip cuttings.

*Time to initiate roots, summer.*—About seven days at temperatures about 22° C.

*Time to initiate roots, winter.*—About ten days at temperatures about 19° C.

*Time to produce a rooted young plant, summer.*—About three weeks at temperatures about 21° C.

*Time to produce a rooted young plant, winter.*—About four weeks at temperatures about 18° C.

*Root description.*—Medium in thickness, fibrous; white to light brown in color.

*Rooting habit.*—Freely branching; dense.

Plant description:

*Plant form and growth habit.*—Relatively compact, upright and somewhat outwardly spreading plant form, broad inverted triangular plant form; moderately vigorous growth habit.

*Branching habit.*—Moderate branching habit, usually about six lateral branches develop; pinching enhances lateral branch development.

*Plant height.*—About 66.5 cm.

*Plant diameter* (*area of spread*).—About 94 cm.

Lateral branch description:

*Length.*—About 51.8 cm.

*Diameter.*—About 8 mm.

*Internode length.*—About 3.6 cm.

*Strength.*—Moderately strong.

*Aspect.*—Erect to about 40° from vertical.

*Texture.*—Smooth, glabrous.

*Color.*—Close to between 138A and 143A.

Leaf description:

*Arrangement.*—Alternate, single.

*Length.*—About 18.8 cm.

*Width.*—About 13.6 cm.

*Shape.*—Ovate, typically palmately-lobed.

*Apex.*—Apiculate.

*Base.*—Cordate.

*Margin.*—Irregularly crenate to bluntly serrate.

*Texture and luster, upper and lower surfaces.*—Smooth, glabrous; matte.

*Venation pattern.*—Pinnate.

*Color.*—Developing leaves, upper surface: Close to N137D. Developing leaves, lower surface: Close to 137C. Fully expanded leaves, upper surface: Close to N137C; venation, close to 144A. Fully expanded leaves, lower surface: Between 146B and 147B; venation, close to 144B.

*Petioles.*—Length: About 14.9 cm. Diameter: About 4 mm. Texture, upper and lower surfaces: Smooth, glabrous. Color, upper and lower surfaces: Close to 144C.

Flower description:

*Flower arrangement.*—Large rotate flowers arranged singly at terminal leaf axils; freely flowering habit with about 66 flowers developing per plant during the flowering season; flowers face mostly outwardly to slightly upright.

*Fragrance.*—None detected.

*Flower longevity.*—Good flower longevity, flowers last for about four days; flowers not persistent.

*Natural flowering season.*—Plants flower from late summer into the autumn in The Netherlands; plants begin flowering about ten weeks after planting.

*Flower diameter.*—About 16.7 cm.

*Flower length* (*height*).—About 6.7 cm.

*Flower buds.*—Length: About 2.8 cm. Diameter: About 2.1 cm. Shape: Ovate. Color: Between 143C and 144A; towards the apex, close to 185D.

*Petals.*—Arrangement: Corolla consists of five petals in a single whorl; petals imbricate. Length: About 8.5 cm. Width: About 9.4 cm. Shape: Broadly obovate. Apex: Rounded. Base: Attenuate. Margin: Entire. Texture, upper and lower surfaces: Smooth, glabrous. Luster, upper and lower surfaces: Slightly glossy; towards the base, moderately glossy. Color: When opening, upper surface: Close to 68B; towards the base, close to 46B; venation, close to 61C. When opening, lower surface: Close to 68B; venation, close to 61B. Fully opened, upper surface: Close to 68B to 68C and becoming closer to 68A with development; towards the base, close to 46B; venation, close to N66A. Fully opened, lower surface: Close to 68B; venation, close to 61B.

*Sepals.*—Appearance: Five sepals fused into a tubular star-shaped calyx. Length: About 3.2 cm. Width:

About 2 cm. Shape: Ovate. Apex: Broadly acute. Margin: Entire. Texture and luster, upper and lower surfaces: Smooth, glabrous; matte. Color: When opening, upper surface: Close to between 138B and 143D. When opening, lower surface: Close to 143C. Fully opened, upper surface: Close to 143C. Fully opened, lower surface: Close to 143B.

*Bracts*.—Quantity per flower: Ten in a single whorl. Length: About 1.9 cm. Width: About 3 mm. Shape: Lanceolate. Apex: Acute. Texture, upper and lower surfaces: Smooth, glabrous. Color, upper surface: Close to 143C. Color, lower surface: Close to 143A.

*Peduncles*.—Length: About 7 cm. Diameter: About 2.5 mm. Strength: Moderately strong. Angle: About 30° from the lateral branch axis. Texture: Smooth, glabrous. Color, upper and lower surfaces: Close to 144A.

*Reproductive organs*.—Androecium: Stamen number: Numerous, about 120. Filament length: About 4 mm. Filament color: Close to 70C to 70D. Anther shape: Orbicular. Anther length: About 2 mm. Anther color: Close to 175A. Amount of pollen: Abundant. Pollen color: Close to 161A to 161B. Gynoecium: Pistil length: About 4.8 cm. Style length: About 4.6 cm. Style color: Close to 70C to 70D. Stigma appearance: Five-parted, club-shaped. Stigma color: Close to 47A. Ovary color: Close to 150C.

*Seeds and fruits*.—Seed and fruit development have not been observed on plants of the new *Hibiscus*.

Temperature tolerance: Plants of the new *Hibiscus* have been observed to tolerate high temperatures of about 35° C. and to be hardy to USDA Hardiness Zone 6.

Pathogen & pest resistance: Plants of the new *Hibiscus* have not been observed to be resistant to pathogens and pests common to *Hibiscus* plants.

It is claimed:

1. A new and distinct *Hibiscus* plant named 'Extrhopin2' as illustrated and described.

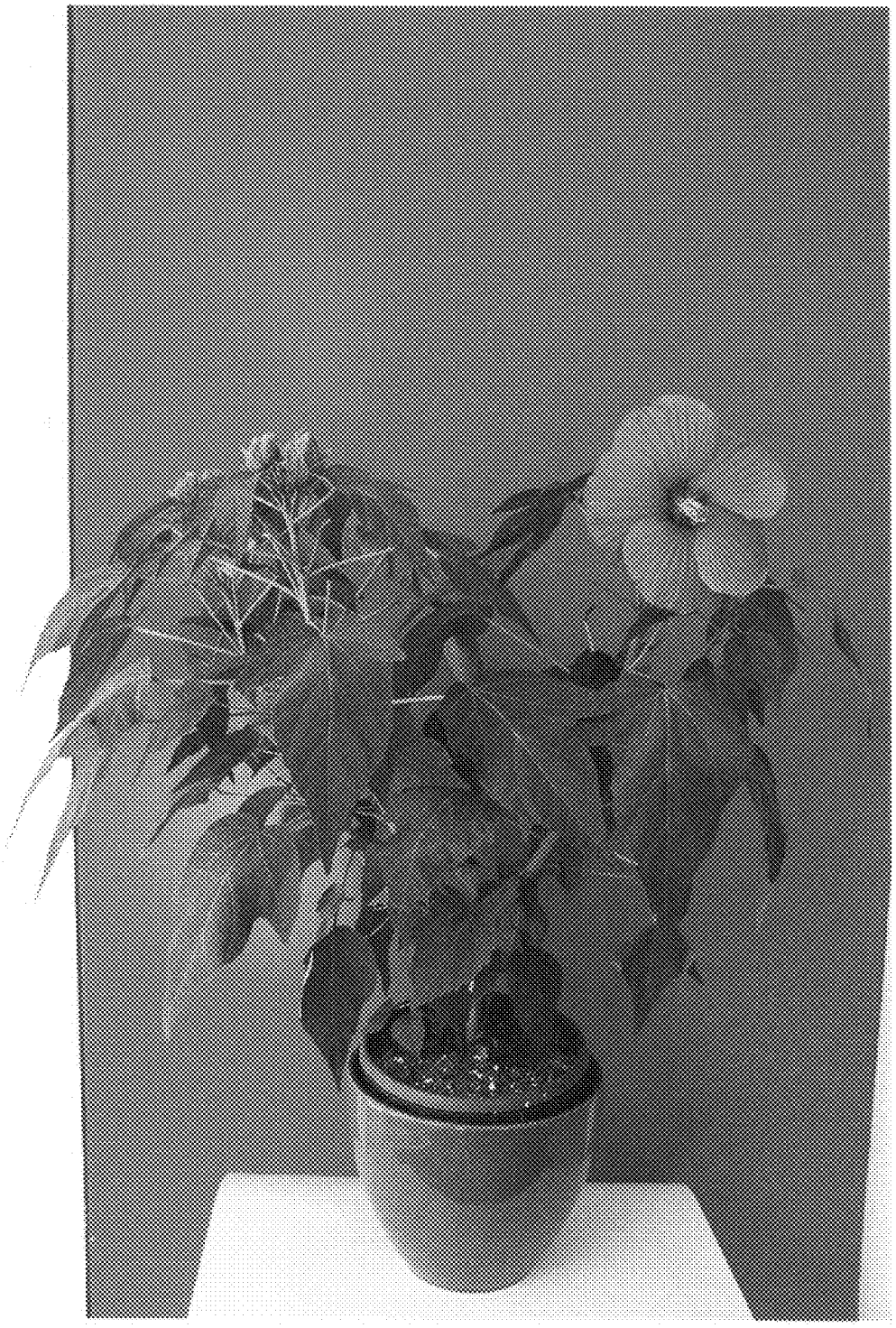

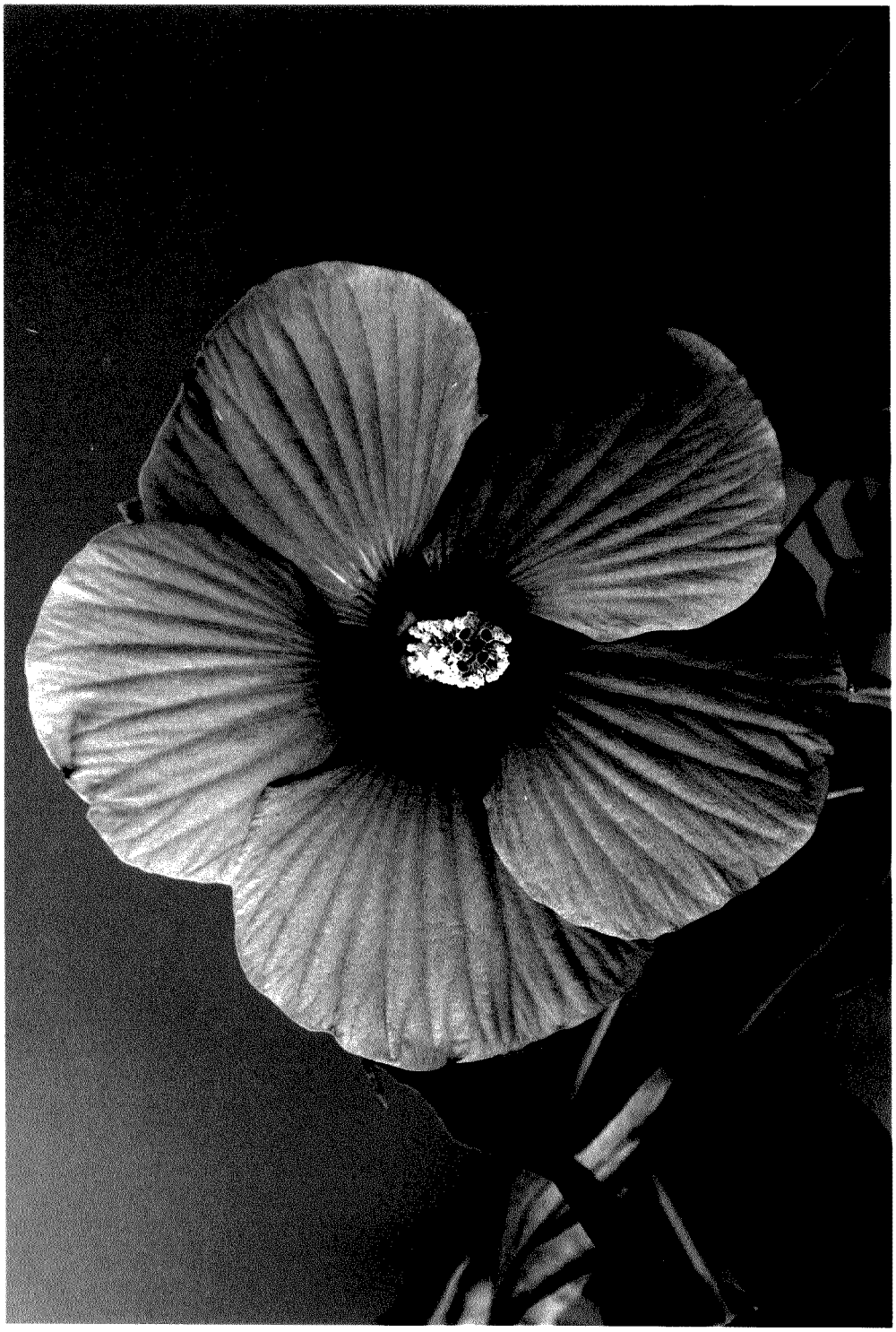

* * * * *